United States Patent [19]

Abraham et al.

[11] 4,244,947
[45] Jan. 13, 1981

[54] CARBA DECAPEPTIDE DERIVATIVES OF [TYR⁶]-SOMATOSTATIN

[75] Inventors: Nedumparampil A. Abraham, Dollard des Ormeaux; Francesco Bellini; Hans U. Immer, both of Mount Royal; Marvin M. Kobric, St. Laurent, all of Canada

[73] Assignee: Ayerst McKenna and Harrison Inc., Montreal, Canada

[21] Appl. No.: 66,258

[22] Filed: Aug. 13, 1979

[51] Int. Cl.³ .................... A61K 37/00; C07C 103/52
[52] U.S. Cl. ............................. 424/177; 260/112.5 S
[58] Field of Search .................. 260/112.5 S; 424/177

[56] References Cited

U.S. PATENT DOCUMENTS

| 4,020,157 | 4/1977 | Immer et al. | 260/112.5 S |
|---|---|---|---|
| 4,115,554 | 9/1978 | Veber | 260/112.5 S |
| 4,161,521 | 7/1979 | Veber et al. | 260/112.5 S |

FOREIGN PATENT DOCUMENTS

| 827530 | 10/1975 | Belgium | 260/112.5 S |
|---|---|---|---|
| 2635558 | 2/1977 | Fed. Rep. of Germany | 260/112.5 S |
| 7602395 | 9/1976 | Netherlands | 260/112.5 S |

OTHER PUBLICATIONS

J. Rivier, et al., "Peptides" 1976 427–451.
J. E. Rivier, et al., J. Med. Chem. 19, 1010 1976.

Primary Examiner—Delbert R. Phillips
Attorney, Agent, or Firm—Arthur E. Wilfond

[57] ABSTRACT

Peptides of formula I

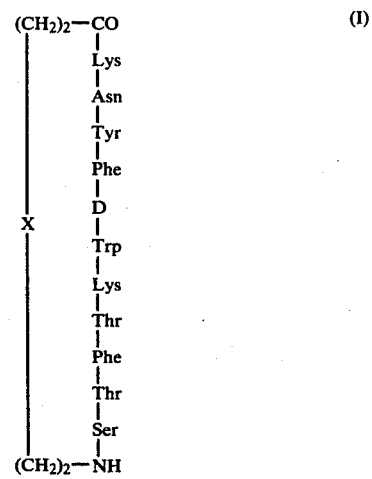

in which X is $(CH_2)_2$, $S-CH_2$ or $CH_2-S$ or a therapeutically acceptable acid addition salt thereof are disclosed. The peptides of formula I are useful as agents for the treatment of acromegaly and the management of diabetes in a mammal. Compositions and methods for the preparation of the peptides of formula I are also disclosed.

7 Claims, No Drawings

CARBA DECAPEPTIDE DERIVATIVES OF [TYR⁶]-SOMATOSTATIN

BACKGROUND OF THE INVENTION

(a) Field of Invention

This invention relates to carba derivatives of the tetradecapeptide somatostatin. More particularly, this invention concerns carba decapeptide derivatives in

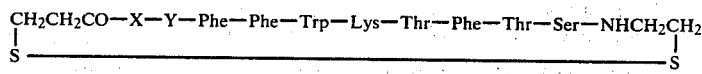

which phenylalanine at position 6 is replaced with tyrosine, the L-tryptophan is replaced with D-trytophan and one or two of the sulfur atoms is replaced with a methylene group and salts thereof, a process for preparing said derivatives and salts, intermediates used in the process, compositions and methods for using the carba decapeptide derivatives and their salts.

(b) Prior Art

The name "somatostatin" has been proposed for the factor found in hypothalamic extracts which inhibits the secretion of growth hormone (somatotropin). The structure of this factor has been elucidated by P. Brazeau et al., Science, 179, 77 (1973) and reported to have the following tetradecapeptide structure:

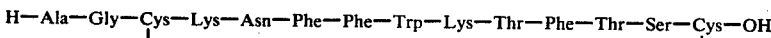

The constitution of the tetradecapeptide somatostatin has been confirmed by synthesis; for example, see D. Sarantakis and W. A. McKinley, Biochem. Biophys. Res. Comm., 54, 234 (1973), J. Rivier et al., Comp. Rend., Ser. D, 276 2737 (1973) and H. U. Immer et al., Helv. Chim. Acta, 57, 730 (1974).

The important physiological activity of this tetradecapeptide established it as a compound of significance for clinical pharmacology relating to the treatment of acromegaly and the management of diabetes; for example, see K. Lundbaek et al., Lancet, 2, 131 (1970) and R. Guillemin in "Chemistry and Biology of Peptides", J. Meienhofer, Ed., 3rd American Peptide Symposium Boston 1972, Ann Arbor Science Publications, Ann Arbor, Mich., 1972.

Since the structure and physiological activity of somatostatin were determined, a number of analogs of somatostatin have been reported, for instance see the report by J. Rivier, et al., in "Peptides 1976", Editions de L'Universite de Bruxelles, Brussels, Belgium, edited by A. Loffet, 1977, pp. 427–451. More specifically, a number of decapeptide derivatives of somatostatin have been reported, for example: Derwent Publications Ltd., Farmdoc 75059X for Netherland patent application Ser. No. 7,602,395, published Sept. 14, 1976, discloses compounds of the formula

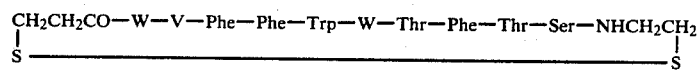

in which X is Lys, Nle or Cys and Y is Asn, Gln or Thr; Derwent Publications Ltd., Farmdoc 70672W for Belgium Pat. No. 827,530 issued Oct. 3, 1975, discloses compounds of the formula

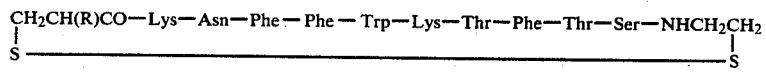

in which V is Asn or Ala and W is Lys or Orn; and by H. U. Immer et al., in U.S. Pat. No. 4,020,147, issued Apr. 26, 1977, discloses compounds of the formula

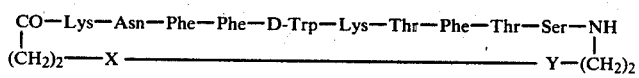

in which R is hydrogen or NHR¹ wherein R¹ is lower aliphatic acyl or benzoyl.

Carba decapeptide derivatives of somatostatin also are known; for example, Derwent Publications Ltd., Farmdoc 13282Y for German patent application No. 2,635,558, published Feb. 17, 1977 discloses peptides of the formula $$CO-Lys-Asn-Phe-Phe-D\text{-}Trp-Lys-Thr-Phe-Thr-Ser-NH$$
$$(CH_2)_2-\!\!\!-X\text{————————————————}Y-(CH_2)_2$$

in which X is $CH_2$, S or $(X)_n$ wherein n is 0 and Y is $CH_2$, S or $(Y)_n$ wherein n is 0; and D. F. Verber in U.S. Pat. No. 4,115,554, issued Sept. 19, 1978 discloses of the formula $$CO-Lys-A-Phe-B-D\text{-}Trp-Lys-C-Phe-D\text{-}E-$$

wherein R is H or COOH; A is $(Asn)_n$ wherein n=0 or 1, α-Abu, Pro or Ala; B is Phe or Tyr; C and D are independently Thr or Val; and E is Ser, Pro, Ala or Gly; wherein at least one of A and E is Pro.

Furthermore, a number of somatostatin derivatives in which a phenylalanine residue is replaced by a tyrosine residue is reported by J. E. Rivier et al., J. Med. Chem., 19, 1010 (1976).

The present invention discloses novel carba decapeptide derivatives of somatostatin in which phenylalanine at position 6 is replaced with tyrosine, the L-tryptophan is replaced with D-tryophan and one or two of the sulfur atoms is replaced with a methylene group. The carba decapeptide derivatives of this invention have a favourable and important separation of the inhibition of insulin and glucagon activities. These decapeptides show a greater inhibition on the release of glucagon than on the release of insulin when compared to somatostatin. This feature makes the decapeptides of this invention especially useful for the treatment of diabetes in a diabetic mammal.

The carba derivatives of this invention are prepared readily by a convenient process, which includes the following advantages: the process starts from readily available materials, avoids noxious reagents, is executed facilely and utilizes easily removable protecting groups.

SUMMARY OF THE INVENTION

The peptides of this invention are replaced by formula I

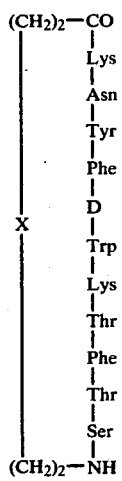  (I)

in which X is $(CH_2)_2$, $S-CH_2$ or $CH_2-S$ or a therapeutically acceptable acid addition salt thereof.

The peptides of formula I or a therapeutically acceptable acid addition salt thereof are prepared by a process which comprises:

cyclizing an acid addition salt of a peptide of formula II

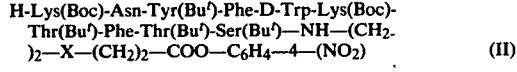 (II)

in which X is as defined herein to obtain the corresponding peptide of formula III

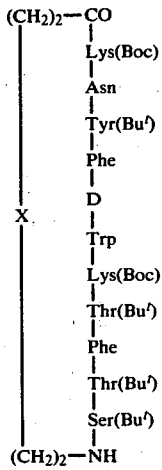  (III)

in which X is as defined herein and deprotecting the latter peptide under moderately acidic conditions to obtain the corresponding peptide of formula I in which X is as defined herein and, if desired, reacting said peptide of formula I with a therapeutically acceptable acid to obtain the therapeutically acceptable acid addition salt of said peptide of formula I.

The peptide of formula II is prepared by a process which comprises:

coupling, according to the azide coupling method, a tetrapeptide of formula Ddz-Lys(Boc)-Asn-Tyr(Bu$^t$)-Phe-NHNH$_2$ with a hexapeptide of formula H-D-Trp-Lys(Boc)-Thr(Bu$^t$)-Phe-Thr(Bu$^t$)-Ser(Bu$^t$)-OMe to obtain the corresponding decapeptide of formula Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)OMe;

reacting the latter decapeptide with hydrazine hydrate to obtain the corresponding decapeptide hydrazide of formula Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)-NHNH$_2$;

condensing, according to the azide coupling method, the latter decapeptide hydrazide with a compound of formula IV, $NH_2-(CH_2)_2-X-(CH_2)_2-COO-Alk$ in which X is as defined herein and Alk is lower alkyl, to obtain the corresponding peptide of formula V, Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_2$—X—(CH$_2$)$_2$—COO—Alk, in which X and Alk are as defined herein;

hydrolyzing the peptide of formula V under alkaline conditions to obtain the corresponding peptide of formula VI, Ddz-Lys(boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_2$—X—(CH$_2$)$_2$—COOH, in which X is as defined herein;

condensing the peptide of formula VI with 4-nitrophenyltrifluoroacetate to obtain the corresponding peptide of formula VII, Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_2$—X—(CH$_2$)$_2$—COO—C$_6$H$_4$—4—(NO$_2$), in which X is as defined herein; and reacting the peptide of formula VII under mildly acidic conditions to obtain the acid addition salt of the correpsonding peptide of formula II.

The peptides of formula I are useful for treating acromegaly or managing diabetes in a mammal by administering to the mammal an effective amount of a peptide of formula I or a therapeutically acceptable acid addition salt thereof.

The peptides of formula I form a pharmaceutical composition which comprises a peptide of formula I, or a therapeutically acceptable acid addition salt thereof, and a pharmaceutically acceptable carrier.

DETAILS OF THE INVENTION

In general the abbreviations used herein for designating the amino acids and the protective groups are based on recommendations of the IUPAC-IUB Commission on Biochemical Nomenclature, see Biochemistry, 11, 1726–1732 (1972). For instance, Ala, Gly, Cys, Lys, Asn, Asp, Phe, Trp, Tyr, D-Trp, Thr and Ser represent the "residues" of L-alanine, glycine, L-cysteien, L-lysine, L-asparagine, L-aspartic acid, L-phenylalanine, L-tryptophan, L-tyrosine, D-trytophan, L-threonine and L-serine, respectively. The term "residue" refers to a radical derived from the corresponding α-amino acid by eliminating the hydroxyl of the carboxyl group and one hydrogen of the α-amino group.

A number of procedures or techniques for the preparation of peptides have hitherto been well established and found in general textbooks of peptide chemistry; for example K. D. Kopple, "Peptides and Amino Acids", W. A. Benjamin, Inc., New York, 1966, pp. 33–51 and E. Schröder and K. L. Lübke, "The Peptides", Vol. I, Academic Press, New York, 1965, pp. 3–128.

For instance, the functional groups which are not involved in the peptide bond formation reaction are protected by a protecting group or groups introduced prior to the condensation reaction. Examples of protecting groups for an amino group not involved in the peptide bond formation are: the urethane type which includes benzyloxycarbonyl (represented by Z), t-butoxycarbonyl (represented by Boc), $\alpha,\alpha$-dimethyl-3,5-dimethoxy-benzyloxycarbonyl (represented by Ddz), 2-(4-biphenyl)-isopropyloxycarbonyl (represented by Bpoc), 4-chlorobenzyloxycarbonyl, 4-methoxybenzyloxycarbonyl, 4-nitrobenzyloxycarbonyl, isonicotinyloxycarbonyl, isobornyloxycarbonyl, isopropyloxycarbonyl, or ethoxycarbonyl; the acyl type protecting groups which include formyl, trifluoroacetyl, phthalyl, acetyl (Ac), nitrophenylsulfenyl, or toluenesulfonyl; the alkyl type protecting groups which include triphenylmethyl (or trityl, represented by Trt), trimethylsilyl or benzyl; the preferred protecting groups in the process of the invention are benzyloxycarbonyl, t-butoxycarbonyl, triphenylmethyl and $\alpha,\alpha$-dimethyl-3,5-dimethoxybenzyloxycarbonyl. The hydroxyl of serine, threonine and tyrosine can be optionally protected by acetyl, tosyl, benzoyl, tert-butyl (represented by Bu$^t$) and benzyl; the preferred protecting group is tert-butyl. The carboxylic acid function of a peptide or amino acid can be considered protected by a lower alkyl or lower aralkyl ester, which include methyl (represented by OMe), ethyl (represented by OEt), t-butyl (represented by OBu$^t$), or benzyl (represented by OBzl) esters; and also by substituted hydrazides, which include t-butoxycarbonyl hydrazide (represented by NHNH-Boc), benzyloxycarbonyl hydrazide (represented by NHNH-Z), or $\alpha,\alpha$-dimethyl-3,5-dimethoxybenzyloxycarbonyl hydrazide (represented by NHNH-Ddz).

A peptide or amino acid is coupled with another peptide or amino acid to form a new peptide by the elimination of water (i.e. dehydrative coupling). More specifically, the hydroxyl portion of a free carboxy group in a peptide or amino acid and a hydrogen atom of the free amino group of the other peptide or amino acid are eliminated to form a new amide bond joining the peptide or amino acid starting materials. To promote facile dehydrative coupling of a peptide free carboxy group with a free amino group of another peptide to form a new peptide bond, the free carboxy group must be activiated. Descriptions of such carboxy activating groups are included in the general textbooks of peptide chemistry by Kopple, or Schröder and Lübke, cited above. Examples of carboxy group activating agents for a carboxylic acid are thionyl chloride, thionyl bromide, methyl chloroformate, a dialkylcarbodiimide (e.g., dicyclohexylcarbodiimide); N-hydroxysuccinimide, 2,4,5-trichlorophenol, pentachlorophenol, 4-nitrophenol or 1-hydroxybenzotriazole in the presence of a dialkylcarbodiimide; and in the case of a hydrazide, the carboxylic group activating agent is nitrous acid. Examples of the activated form of the terminal carboxy group are acid chloride, anhydride, azide, activated ester, or O-acyl urea of a dialkylcarbodiimide. The following activated esters have proved to be particularly suitable in the process of this invention: 2,4,5-trichlorphenyl (represented by OTcp), pentachlorophenyl (represented by OPep), 4-nitrophenyl (represented by ONp), or 1-benzotriazolyl; the succinimido group is also useful for such activation.

The coupling of a peptide or amino acid, having the activated carboxy group, with another peptide or amino acid having a free amino group is conducted in an inert organic solvent at a temperature from $-30°$ C. to about 50° C. For coupling to occur, the amino group must not be protonated. A sufficient amount of an organic proton acceptor is added to the above reaction mixture until the amino group is no longer protonated (usually pH 7.0 to 8.0).

The term "azide coupling method" as used herein refers to the method of activating the terminal carboxy of a peptide fragment as an azide and condensing the latter peptide azide with another peptide having a free amino group. The peptide azide is conveniently prepared by reacting a peptide hydrazide with a reagent which furnishes nitrous acid in situ. Suitable reagents for this purpose include organic nitrites (e.g. t-butyl nitrite and isoamyl nitrite) or alkali metal nitrite salts (e.g. sodium nitrite and potassium nitrite) in the presence of a mineral acid, such as hydrogen chloride or sulfuric or phosphoric acid. The corresponding peptide azide thus obtained is then reacted with a peptide or compound having a free amino group to obtain the desired peptide. Preferred conditions for the azide method of coupling comprises reacting the peptide hydrazide with nitrous acid, generated in situ from an organic nitrite in the presence of a strong acid, preferably hydrogen chloride (pH ranging usually from 0.1 to 2), in an anhydrous inert organic solvent, for example, dimethylformamide, dimethyl sulfoxide, ethyl acetate, methylene dichloride, tetrahydrofuran, dioxane, and the like at $-30°$ C. to 20° C., preferably at about $-20°$ C. to $-5°$ C. for 10 to 30 minutes to obtain the corresponding azide. The peptide azide can be isolated and crystallized but is preferably allowed to remain in the reaction mixture. Thereafter the azide in the above mixture is reacted with one to two molar equivalents of the peptide unit or compound having the free amino group at temperatures ranging from $-30°$ to 20° C. for about one to two hours and then at 0° to 30° C. for 10 to 30 hours. An acid acceptor, preferably an organic proton acceptor, for example N-ethyldiisopropylamine, N-ethylmorpholine or triethylamine, is present in the reaction mixture in order to make the reaction medium slightly alkaline, preferably pH 7.0 to 9.0. See also the above cited textbooks of Kopple or Schröder and Lübke for additional descriptions of this method.

The terms peptide, polypeptide, tripeptide, hexapeptide, and the like as used herein are not limited to refer to the respective parent peptides but are also used with reference to modified peptides with or without functionalized or protecting groups. The term "peptide" as used herein is used with reference to a peptide with two to ten amino acid residues.

The abbreviation Me represents a methyl group, $NHNH_2$ represents a hydrazide group and $N_3$ represents an azide group.

The term "lower alkyl" as used herein means hydrocarbon radicals having one to three carbon atoms and includes methyl, ethyl and propyl.

The term "lower alkanol" as used herein means monohydric alcohols having one to four carbon atoms in a straight or branched chain and includes methanol, ethanol, isopropanol and butanol.

The term "mineral acid" as used herein means the strong inorganic acids and includes hydrochloric, hydrobromic, sulfuric, or phosphoric acid. When the term is used in conjunction with an anhydrous system, anhydrous hydrogen chloride is the preferred mineral acid.

The term "mildly acidic conditions" as used herein means conditions in which an aqueous solution of an organic acid, for example 30-80% aqueous formic, acetic or propionic acid, preferably 70-80%, or mixtures thereof, is a principal component of the reaction medium.

The term "moderately acidic conditions" as used herein means con-as a principal component of the reaction medium at temperatures ranging from about $-30°$ to 30° C. Examples of preferred conditions in this case include the use of 50 to 100% trifluoroacetic acid at 0° to 30° C., 0.1-12 N hydrochloric acid in aqueous solution or in solution in an organic solvent at $-10°$ to 10° C., or hydrogen chloride in solution in anhydrous organic solvents at $-20°$ to 10° C.

The term "organic nitrile" means the lower alkyl nitrites, for instance, t-butyl nitrite, isoamyl nitrite, and the like.

The term "organic proton acceptor" as used herein includes triethylamine, N-ethylmorpholine, N-ethyldiisopropylamine, pyridine and the like.

The peptides of formula I are obtained in the form of the free base or as an acid addition salt directly from the process of this invention. The peptides in the form of the free bases are readily obtained from the corresponding acid addition salt by conventional methods, for example a solution of the acid addition salt is passed through an anionic exchange resin (OH$^-$ form) to obtain the free base. The free base is also obtained from the acetic acid addition salt by repeated lyophilization of the latter salt from aqueous solution. The acetic acid addition salt is readily obtained from another acid addition salt by treatment with the appropriate ion exchange resin in the manner hereinafter disclosed. The peptides of formula I are obtained in the form of a therapeutically acceptable acid addition salt either directly from the process of this invention or by reacting the peptide with one or more equivalents of the appropriate acid. Examples of preferred non toxic salts are those with therapeutically acceptable organic acids, e.g. acetic, lactic, succinic, benzoic, salicyclic, methanesulfonic, toluenesulfonic, or pamoic acid, as well as polymeric acids such as tannic acid or carboxymethyl cellulose, and salts with inorganic acids such as the hydrohalic acids, e.g. hydrochloric acid, or sulfuric acid, or phosphoric acid. If desired, a particular acid addition salt is converted into another acid addition salt, e.g., a salt with a non toxic, pharmaceutically acceptable acid, by treatment with the appropriate ion exchange resin in the manner described by R. A. Boissonas et al., Helv. Chim. Acta, 43, 1349 (1960). Suitable ion exchange resins are cellulose based cation exchangers, for example carboxymethylcellulose, or chemically modified, cross-linked dextran cation exchangers, for example those of the Sephadex C type, and strongly basic anion exchange resins, for example those listed in J. P. Greenstein and M. Winitz "Chemistry of the Amino Acids", John Wiley and Sons, Inc., New York and London, 1961, Vol. 3, p. 1456.

The in vivo activity of the peptide of formula I is established by subjecting the peptide of formula I, in which X is $(CH_2)_2$ as a representative peptide of this invention, to the following standard test procedures.

Male Sprague Dawley rats (200±10 gm) body weight are used throughout these studies. They are maintained on an ad libitum diet of Purina Lab Chow and tap water until 24 hr before the studies are carried out. In the 24 hr period prior to use, the animals are fasted, but have unlimited access to tap water. All studies are conducted on sodium pentobarbital, sold under the trademark Nembutal, (Abbott Labs, Montreal), 60 mg/kg, ip, anaesthetized rats.

In studies where both insulin and glucagon secretion are investigated, arginine (arginine-HCl in 0.9% aqueous sodium chloride, pH 7.4, 200 mg/100 gm rat, Nutritional Biochemicals, Cleveland) is infused into an exposed jugular vein (2.0 ml/30 min). Blood samples are drawn into heparin (Roussel UCLAF, 1000 units/ml) washed syringes immediately before the infusion began (0 min) and at the termination of the infusion (30 min) from the jugular vein and the inferior venae cava, respectively.

In studies where only insulin secretion is stimulated, glucose in 0.9% aqueous sodium chloride (British Drug House, Poole, England) is infused into an exposed jugular vein (100 mg/100 gm, in a volume of 2.0 ml for 30 min). Blood is collected from the inferior vena cava at the termination of the infusion (30 min) into heparin washed syringes.

The peptide of formula I or somatostatin at various concentrations is infused simultaneously with the arginine or glucose stimulus, with the aid of a butterfly infusion set (23 guage) into the test animals. The effect of the vehicle on the release of the hormones is determined by infusing the saline diluent into selected rats.

The blood samples are discharged into chilled (4° C.) glass test tubes, containing aprotinin, sold under the trademark Trasylol, (Boehringer Ingelheim, Montreal), 500 KIU/ml whole blood, and plasma samples were collected after centrifugation (4° C., 3000 rpm for 30 min). The plasma samples were stored at $-20°$ until assayed for immuno reactive glucagon (IRG) using antiserum 30 K and for immuno reactive insulin (IRI) by the methods described by W. Lippmann and M. Kobric, Horm. Metab. Res., 10, 280 (1978).

All results are expressed as the mean ±SEM of the response. Insulin and glucagon responses obtained in the arginine treated groups are derived by subtracting the basal hormone level from the level at 30 min, and are expressed in Tables I, II and III as $\Delta$IRG (pg/ml) and $\Delta$IRI/($\mu$U/ml), for glucagon and insulin, respectively. Insulin results obtained from the glucose treated animals are in absolute hormone level at the termination of the infusion.

Wilcoxon's two sample test for unpaired observations, as described in "Statistical Methods", G. W. Snedecor and W. G. Cochran, ed., sixth edition, the Iowa State University Press, Ames, Iowa, 1973, pp 130 and 131, is used to determine the significance of the peptide+arginine or peptide+glucose versus the responses due to arginine or glucose alone. In selected instances, parallel dose-response line assay by analysis of variance, as described in "Statistical Method in Biological Assay", D. J. Finney, ed., second edition, Hafner Publishing Company, New York, 1964, is used to determine the relative potency of the 2 peptides in the bioassays. A $p \leq 0.05$ is deemed to be significant.

Table I indicates that somatostatin suppresses IRI at a lower dose than does the peptide of formula I in which X is $(CH_2)_2$.

Table II illustrates the IRG responses to the infusion of arginine in the absence and in the presence of peptides. Both somatostatin and the peptide of formula I in which X is $(CH_2)_2$ suppresses the IRG secretion about equally.

Table III illustrates that somatostatin is significantly more potent than the peptide of formula I in which X is $(CH_2)_2$ in suppressing IRI secretion on glucose insulin secretion.

From the data given in Tables I, II and III, it is found that the peptide of formula I in which X is $(CH_2)_2$, administered in the range of about 200 to 400 μg/kg, reduces glucagon markedly without drastically changing the insulin concentration, thereby providing a decided advantage in treatment of diabetes, where better blood glucose control may be obtained by avoiding insulin suppression.

The peptides of formula I give complex salts with heavy metal ions. An example of a pharmaceutically acceptable heavy metal complex is a complex formed with zinc or with zinc protamine.

The peptides of formula I, or the salts thereof are useful for the treatment of acromegaly and related hypersecretory endocrine states and in the management of diabetes in mammals; see for example, P. Brazeau et al., cited above. When the peptides or salts thereof are employed for such treatment or management, they are administered systemically, preferably parenterally, in combination with a pharmaceutically acceptable liquid carrier. The peptides of formula I have a low order of toxicity. The proportion of the peptide or salt thereof is determined by its solubility in the given carrier, by the given carrier, or by the chosen route of administration. When the peptide or a salt thereof is used in a sterile aqueous solution, such solution may also contain other solutes such as buffers or preservatives, as well as sufficient amounts of pharmaceutically acceptable salts or glucose to make the solution isotonic. The dosage will vary with the form of administration and with the particular species to be treated and is preferably kept at a level of from 1 mcg to 300 mcg per kilogram body weight per day. However, a dosage level in the range of from about 1 mcg to about 50 mcg per kilogram body weight per day is most desirably employed in order to achieve effective results.

TABLE I

The effects of somatostatin and the peptide of formula I in which X is $(CH_2)_2$ on arginine stimulated insulin secretion

| Treatment | Dose[1] | $\Delta IRI(\mu U/ml)^{2,5}$ | p[3] |
|---|---|---|---|
| Study A | | | |
| vehicle | — | 4.7 ± 0.6(12)[4] | — |
| arginine | — | 80.2 ± 22.9(6) | — |
| arginine + somatostatin | 0.3 | 73.8 ± 18.5(6) | NS |
| | 1.0 | 43.0 ± 22.6(6) | NS |
| | 3.0 | 40.0 ± 6.6(6) | NS |
| | 30.0 | 23.2 ± 12.5(6) | <0.05 |
| arginine + peptide[6] | 0.3 | 74.8 ± 16.1(6) | NS |
| | 1.0 | 78.6 ± 16.9(5) | NS |
| | 3.0 | 78.2 ± 16.0(5) | NS |
| | 30.0 | 40.7 ± 8.3(6) | NS |
| Study B | | | |
| vehicle | — | 6.9 ± 9.1(12) | — |
| arginine | — | 77.6 ± 5.2(12) | — |
| arginine + somatostatin | 0.03 | 88.3 ± 9.1(6) | NS |
| | 0.3 | 76.8 ± 5.2(5) | NS |
| | 3.0 | 32.2 ± 3.5(6) | <0.1 |
| | 30.0 | 35.5 ± 7.8(6) | <0.05 |

TABLE I-continued

The effects of somatostatin and the peptide of formula I in which X is $(CH_2)_2$ on arginine stimulated insulin secretion

| Treatment | Dose[1] | $\Delta IRI(\mu U/ml)^{2,5}$ | p[3] |
|---|---|---|---|
| arginine + peptide[6] | 0.03 | 62.9 ± 14.4(6) | NS |
| | 0.3 | 68.6 ± 20.7(6) | NS |
| | 3.0 | 114.4 ± 11.2(5) | NS |
| | 30.0 | 97.8 ± 22.8(6) | NS |
| Study C | | | |
| vehicle | — | 25.2 ± 5.5(6) | — |
| arginine | — | 101.7 ± 21.2(6) | — |
| arginine + somatostatin | 10.0 | 52.8 ± 9.3(6) | <0.05 |
| | 100.0 | 25.5 ± 8.1(6) | <0.01 |
| arginine + peptide[6] | 10.0 | 93.8 ± 7.1(6) | NS |
| | 100.0 | 38.0 ± 10.6(6) | <0.05 |

[1] μg peptide/100 gm body weight rat.
[2] mean incremental change of IRI from basal (μU IRI/ml at 30 min −μU IRI/ml at 0 min).
[3] p level as determined by rank test vs arginine alone.
[4] numbers in brackets indicate number of observations per group.
[5] all results expressed as mean ± SEM.
[6] peptide of formula I in which X is $(CH_2)_2$.

TABLE II

The effect of somatostatin and the peptide of formula I in which X is $(CH_2)_2$ on arginine stimulated glucagon secretion

| Treatment | Dose[1] | $\Delta IRG(pg/ml)^{2,5}$ | p[3] |
|---|---|---|---|
| Study A | | | |
| vehicle | — | −1.8 ± 7.7(12)[4] | — |
| arginine | — | 268.5 ± 18.4(12) | — |
| arginine + somatostatin | 0.3 | 157.2 ± 35.9(6) | <0.05 |
| | 1.0 | 72.7 ± 19.0(6) | <0.01 |
| | 3.0 | 102.5 ± 25.8(6) | <0.01 |
| | 30.0 | 90.2 ± 38.4(5) | <0.05 |
| arginine + peptide[6] | 0.3 | 151.5 ± 27.5(5) | <0.05 |
| | 1.0 | 100.4 ± 30.4(5) | <0.01 |
| | 3.0 | 109.3 ± 44.4(4) | <0.05 |
| | 30.0 | 40.0 ± 25.0(6) | <0.01 |
| Study B | | | |
| vehicle | — | 17.8 ± 3.6(12) | — |
| arginine | — | 229.9 ± 21.8(12) | — |
| arginine ± somatostatin | 0.03 | 211.0 ± 23.1(4) | NS |
| | 0.3 | 149.2 ± 29.9(6) | NS |
| | 3.0 | 69.3 ± 22.2(6) | <0.01 |
| | 30.0 | 69.7 ± 8.4(6) | <0.01 |
| arginine + peptide[6] | 0.03 | 157.8 ± 30.6(6) | <0.05 |
| | 0.3 | 132.2 ± 20.9(5) | <0.05 |
| | 3.0 | 105.7 ± 22.7(6) | <0.01 |
| | 30.0 | 49.3 ± 14.4(6) | <0.01 |

[1] μg peptide/100 gm rat infused for 30 min
[2] mean incremental change of plasma IRG from level at 0 min to level at 30 min
[3] significance of levels of IRG of peptide treated group vs levels of arginine treated animals, rank test
[4] numbers in brackets indicate observations per treatment group
[5] all results are in terms of mean ± SEM of group
[6] peptide of formula I in which X is $(CH_2)_2$

TABLE III

The effect of somatostatin and the peptide of formula I in which X is $(CH_2)$ 2 on glucose stimulated insulin secretion

| Treatment | Dose[1] | $IRI/ml^2$ | p[3] |
|---|---|---|---|
| Study A | | | |
| glucose | — | 77.2 ± 13.5(6)[4] | — |
| glucose + somatostatin | 10 | 27.2 ± 4.7(6) | <0.05 |
| | 100 | 12.3 ± 3.9(6) | <0.01 |
| glucose + peptide[5] | 10 | 47.2 ± 9.8(6) | NS |
| | 100 | 13.7 ± 0.8(6) | 0.01 |
| Study B | | | |
| vehicle | — | 9.3 ± 2.1(6) | — |
| glucose | — | 89.2 ± 8.4(6) | — |
| glucose + somatostatin | | | |

TABLE III-continued

The effect of somatostatin and the peptide of formula
I in which X is $(CH_2)_2$ on glucose stimulated insulin secretion

| Treatment | Dose[1] | IRI/ml[2] | p[3] |
|---|---|---|---|
| | 10 | 40.3 ± 7.7(6) | <0.01 |
| | 30 | 17.0 ± 7.5(6) | <0.01 |
| | 100 | 6.2 ± 1.9(6) | <0.01 |
| glucose + peptide[5] | | | |
| | 10 | 63.8 ± 5.1(6) | NS |
| | 30 | 40.2 ± 6.8(6) | <0.01 |
| | 100 | 32.8 ± 11.4(6) | <0.01 |

[1]μg peptide/100 gm rat infused for 30 min
[2]means ± SEM of level observed at 30 min
[3]significance of levels in peptide treated group vs glucose alone, rank test
[4]numbers in brackets indicate observations in treatment group
[5]peptide of formula I in which X is $(CH_2)_2$ The peptides of formula I or salts thereof may also be administered in one of the long-acting, slow-release or depot dosage forms described below, preferably by intramusclar injetion or by implantation. Such dosage forms are designed to release from about 0.1 mcg to about 50 mcg per kilogram body weight per day, and may contain either a pharmaceutically acceptable salt of the peptide having a low degree of solubility in body fluids, for example one of those salts described below, or the peptide in the form of a water-soluble salt together with a protective carrier, which prevents rapid release. In the latter case, for example, the peptide may be formulated with a non-antigenic partially hydrolyzed gelatin in the form of a viscous liquid; or the peptide may be absorbed on a pharmaceutically acceptable solid carrier, for example, zinc hydroxide, and may be administered in suspension in a pharmaceutically acceptable liquid vehicle; or the peptide may be formulated in gels or suspensions with a protective non-antigenic hydrocolloid, for example sodium carboxymethylcellulose, polyvinylpyrrolidone, sodium alginate, gelatin, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, 14th Ed., Mac Publishing Co., Easton, Pennsylvania, 190. Long-acting, slow-release preparations of the peptide, produced according to the process of this invention, may also be obtained by microencapsulation in a pharmaceutically acceptable coating, for example, gelatin, polyvinyl alcohol or ethyl cellulose. Further examples of coating materials and of the processes used for microencapsulation are described by J. A. Herbig in "Encyclopedia of Chemical Technology", Vol. 13, 2nd ed., Wiley, New York 1967, pp. 436–456. Such formulations, as well as suspensions of salts of the peptide, which are only sparingly soluble in body fluids, for example salts with pamoic acid or tannic acid, are designed to release from about 1.0 mcg to about 100 mcg of the active compound per kilogram body weight per day, and are preferably administered by intramuscular injection. Alternatively, some of the solid dosage forms listed above, for example certain sparingly water-soluble salts or dispersions in a neutral hydrogel of a polymer of ethylene glycol metharcrylate or similar monomers cross-linked as described in U.S. Pat. No. 3,551,556, may also be formulated in the form of pellets releasing about the same amounts as shown above and may be implanted subcutaneously or intramuscularly.

PROCESS

The first starting tetrapeptide Ddz-Lys(Boc)-Asn-Tyr(Bu$^t$)-Phe-NHNH$_2$, is prepared by the successive dehydrative coupling of the appropriate amino acid derivatives. The first step, for the preparation of this tetrapeptide, is the condensation of Z-Tyr(Bu$^t$)-OH with H-Phe-OMe to obtain Z-Tyr(Bu$^5$)-Phe-OMe. The condensation is preferably achieved by reacting Z-Tyr(Bu$^t$)-OH with about a molar equivalent of each of H-Phe-OMe, dicyclohexylcarbodiimide, and 1-hydroxybenzotriazole and sufficient organic proton acceptor, e.g. N-ethylmorpholine, to obtain a neutral solution in an inert organic solvent, preferably dimethylformamide, at 10° to 30° C. for 15 to 30 hours. Removal of the α-amino protecting group from Z-Tyr(Bu$^t$)-Phe-OMe, preferably by hydrogenation in the presence of a noble metal hydrogenation catalyst, e.g. 5% palladium on carbon, in acetic acid at 20° to 30° C. gives H-Tyr(Bu$^t$)-Phe-OMe acetate. Coupling of the latter dipeptide with about a molar amount of an active ester of Z-Asn-OH, preferably as the 4-nitrophenyl ester and sufficient organic proton acceptor (i.e. N-ethylmorpholine) to obtain a neutral solution in an inert organic solvent (i.e. dimethylformamide) at 0° to 10° C. for two to five days, affords Z-Asn-Tyr(Bu$^t$)-Phe-OMe. The α-amino protecting group is removed from the latter tripeptide, in the same manner as described above, to obtain H-Asn-Tyr(Bu$^t$)-Phe-OMe acetate. This tripeptide is coupled with Ddz-Lys(Boc)-OH, preferably in the same manner as described above for the coupling of Z-Tyr(Bu$^t$)-OH and H-Phe-OMe, to obtain Ddz-Lys(Boc)-Asn-Tyr(Bu$^t$)-Phe-OMe. Reaction of the latter peptide with 20 to 50 molar equivalents of hydrazine hydrate in an inert solvent, preferably methanol, at 20° to 30° C. for 15 to 30 hours gives the tetrapeptide hydrazide, Ddz-Lys(Boc)-Asn-Tyr(Bu$^t$)-Phe-NHNH$_2$.

The hexapeptide starting material of formula H-D-Trp-Lys(Boc)-Thr(Bu$^t$)-Phe-Thr(Bu$^t$)-Ser(Bu$^t$)-OMe is prepared by the successive dehydrative coupling of the appropriate amino acid derivatives. For this preparation, the α-amino protecting group, Z, is removed from the pentapeptide, Z-Lys(Boc)-Thr(Bu$^t$)-Phe-Thr(Bu$^t$)-Ser(Bu$^t$)-OMe, described by H. U. Immer et al., U.S. Pat. No. 3,917,578, issued Nov. 4, 1975, by hydrogenation in the same manner as described above to afford H-Lys(Boc)-Thr(Bu$^t$)-Phe-Thr(Bu$^t$)-Ser(Bu$^t$)-OMe acetate. Condensation of this pentapeptide with about 1.0 to 1.5 molar equivalents of Z-D-Trp-OH, preferably in the same manner as described above for the coupling of Z-Tyr(Bu$^t$)-OH and H-Phe-OMe, yields the hexapeptide Z-D-Trp-Lys(Boc)-Thr(Bu$^t$)-Phe-Thr(Bu$^t$)-Ser(Bu$^t$)-OMe. Removal of the Z protecting group by hydrogenation in the same manner as described above gives the hexapeptide H-D-Trp-Lys(Boc)-Thr(Bu$^t$)-Phe-Thr(Bu$^t$)-Ser(Bu$^t$)-OMe.

Condensation of the tetrapeptide hydrazide Ddz-Lys(Boc)-Asn-Tyr(Bu$^t$)-Phe-NHNH$_2$ with the hexapeptide H-D-Trp-Lys(Boc)-Thr(Bu$^t$)-Phe-Thr(Bu$^t$)-Ser(Bu$^t$)-OMe using the azide coupling method gives the corresponding decapeptide Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)-OMe. A preferred method of achieving this azide coupling is as follows. The tetrapeptide hydrazide is dissolved in an inert organic solvent, preferably dimethylformamide, and the mixture is cooled to about −20° to −10° C. A solution of about two to five molar equivalents of a mineral acid in an inert organic solvent, preferably three molar equivalents of hydrogen chloride in ethyl acetate, is added to the above solution, followed by 1.0 to 1.5 molar equivalents of an organic nitrite, for example, 1.1 to 1.3 molar equivalents of t-butyl nitrite. The solution is stirred at −20° to −10° C. for 10 to 20 minutes to obtain a solution containing the tetrapeptide azide, Ddz-Lys(Boc)-Asn-Tyr(Bu$^t$)-Phe—N$_3$. An organic proton acceptor, preferably N-ethyldiisopropylamine, is added until pH 7.1 to 9 is attained. The mixture is cooled to about −30° to −20° C. and a solution of substantially one molar equivalent of the hexapeptide in an inert organic solvent, preferably dimethylformamide, is added to the above solution containing the azide. If required, the solution is adjusted to pH 7.1 to 9 with the organic proton acceptor. The reaction mixture is then stirred at about −20° to −10° C. for one to two hours and then at about 20° to 30° C. for 20 to 30 hours. The resulting decapeptide Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)-OMe is then isolated by conventional methods, for example, evaporation, precipitation, chromatography and/or crystallization.

This decapeptide is readily converted to the corresponding decapeptide hydrazide of formula Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NHNH$_2$ by hydrazinolysis, which is carried out by dissolving the decapeptide in an inert organic solvent, preferably dimethylformamide, and adding an excess of hydrazine hydrate, for example 10 to 30 molar equivalents. After stirring at about 20° to 30° C. for four to six days, the decapeptide hydrazide is isolated by conventional means.

The aforementioned decapeptide hydrazide and the compound of formula IV, NH$_2$—(CH$_2$)$_2$—X—(CH$_2$)$_2$—COO-Alk in which X and Alk are as defined herein, are coupled according to the azide coupling method, in the same manner as described hereinabove, to obtain the corresponding peptide of formula V, Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_2$—X—(CH$_2$)$_2$—COO-Alk in which X and Alk are as defined herein.

Alkaline hydrolysis of the peptide of formula V gives the corresponding peptide of formula VI, Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_2$—X—(CH$_2$)$_2$—COOH in which X is as defined herein. Preferred conditions for the alkaline hydrolysis is the reaction of the peptide of formula V with 5 to 20 molar equivalents of sodium or potassium hydroxide in an aqueous lower alkanol, preferably methanol or ethanol, at 15° to 30° C. for 20 to 50 hours.

In the next step, the peptide of formula VI is converted to the corresponding active ester of formula VII, Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_2$—X—(CH$_2$)$_2$—COO—C$_6$H$_4$—4-(NO$_2$) in which X is as defined herein, by reacting the peptide of formula VI with 5 to 20 molar equivalents of 4-nitrophenyl trifluoroacetate and 30 to 100 molar equivalents of an organic proton acceptor, preferably pyridine, in an inert organic solvent, preferably dimethylformamide, at 40° to 60° C. for 30 to 100 minutes.

Reaction of the peptide of formula VII under mildly acidic conditions removes the α-amino protecting group (Ddz) whereby the acid addition salt of the corresponding peptide of formula II, H-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_2$—X—(CH$_2$)$_2$—COO—C$_6$H$_4$—4—(NO$_2$) in which X is as defined herein, is obtained. A preferred mildly acidic condition involves the use of an aqueous solution containing 60 to 80 percent acetic acid and 5 to 15 percent formic acid. The peptide of formula VII is allowed to remain in this solution at 15° to 30° C. for 10 to 40 hours and the peptide of formula II is isolated as the formate salt.

The peptide of formula II is cyclized to obtain the corresponding peptide of formula III,

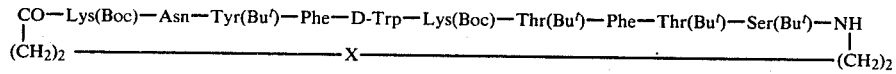

in which X is as defined herein. For this cyclization, the peptide of formula II as an acid addition salt is reacted with a minimum of about three molar equivalents of an organic proton acceptor, preferably pyridine or triethylamine, at 30° to 60° C. for one to five hours, after which the corresponding compound of formula III is isolated. An inert organic solvent, for example, dimethylformamide, dimethylsulfoxide and the like, can be used in the cyclization or an excess of the organic proton acceptor can serve as solvent.

Finally, the aforementioned peptide of formula III is deprotected to the corresponding peptide of formula I in which X is as defined herein by subjecting the former to moderately acidic conditions whereby the remaining protecting groups on the peptide of formula III are removed. Generally this step is carried out by dissolving the cyclic compound in trifluoroacetic acid or in an aqueous reaction medium containing a mineral acid at 0° to 20° C. for 10 to about 60 minutes. Examples of such media are 50 to 100% trifluoroacetic acid, 10 to 20% aqueous sulfuric acid, 10% phosphoric acid, 10 to 30% hydrobromic acid and 10 to 30% hydrochloric acid. An extremely useful medium is trifluoroacetic acid or concentrated hydrochloric acid. Preferred conditions for the present step include dissolving the cyclic peptide of formula III in a small amount of concentrated hydrochloric acid cooled to 0° C. and allowing the mixture to stand at 0° to 5° C. for five to ten minutes under a nitrogen atmosphere. Thereafter, about 5 to 15 volumes of glacial acetic acid is added and the solution is cooled to about −70° C. and lyophilized to give the cyclic peptide of formula I as the hydrochloride salt. Alternatively, the peptide of formula III is dissolved in a solution of trifluoroacetic acid-anisol (10:1 v/v) at 20° to 30° C. and the mixture is allowed to stand at 20° to 30° C. for 30 to 100 minutes under a nitrogen atmosphere. The solution is evaporated to obtain a residue containing the cyclic peptide of formula I as the trifluoroacetate salt.

If required, the above peptides of formula I can be purified by a variety of methods, for example, trituration with an appropriate solvent or by chromatographic methods. A useful solvent for trituration is the upper phase of butanol-acetic acid-water (4:1:5 v/v) wherein the impurities are dissolved in this solvent. For purification by chromatography, a number of chromatographic adsorbents can be used, for example, silica gel, ion exchange adsorbents and partition adsorbents.

When silica gel is used, a suitable solvent for elution of the compound of formula I is a solution of chloroform-methanol-acetic acid-water (15:9:1:2 v/v). Purification by ion exchange chromatography, preferably using a carboxymethyl cellulose cation exchanger and aqueous ammonium acetate as the eluant, gives the peptide of formula I in the form of its acid addition salt with acetic acid. Alternatively, the product is purified by partition chromatography on a chemically modified cross-linked dextran; for example, Sephadex LH-20 using methanol as the eluant, and obtaining the product as the free base, or alternatively using Sephadex G-25 and eluting with the upper phase of butanol-acetic acid-water (4:1:5 v/v) and obtaining the peptide of formula I in the form of its acid addition salt with acetic acid. Also, if desired, a combination of the above chromatographic methods can be used.

The free base of the peptide of formula I can be obtained by repeated lyophilization of the acetic acid addition salt of the peptide of formula I from water.

The following examples illustrate further this invention.

EXAMPLE 1

BENZYLOXYCARBONYL-(O-t-BUTYL)TYROSYL-PHENYLALANINE METHYL ESTER (Z-Tyr(Bu$^t$)-Phe-OMe)

Aqueous sodium hydroxide (1 N, 15 ml, 15 mmoles) was added to an ice-cold solution of Z-Tyr(Bu$^t$)-OMe (3.85 g, 10 mmoles) in methanol (20 ml) and the mixture was stirred at 0° to 50° C. for one hr. After completion of the reaction, the solution was acidified with 10% aqueous citric acid, diluted with water (100 ml) and extracted with ethyl acetate. The organic layer was washed several times with water and dried over anhydrous sodium sulfate. Evaporation of the solvent gives Z-Tyr(Bu$^t$)-OH in quantitative yield, which was used as such in the next step. The latter acid and 1-hydroxybenzotriazole (1.62 g, 12 mmoles) were dissolved in dry, distilled dimethylformamide (30 ml), the solution was cooled to 0° C. and dicyclohexylcarbodiimide (2.48 g, 12 mmoles) was added. The mixture was stirred 1 hr at 0° C. and 1 hr at room temperature and a solution of H-Phe-OMe.HCl (2.58 g, 12 mmoles) in dimethylformamide (35 ml) containing N-ethylmorpholine (1.6 ml, 13 mmoles) was added at 0° C. The mixture was stirred at room temperature overnight. After filtering, the filtrate was evaporated and the residue was dissolved in ethyl acetate. The solution was washed with 5% aqueous citric acid, water, saturated NaHCO$_3$ solution and water, dried over sodium sulfate and evaporated. The residue was crystallized twice from methanol-isopropyl ether giving 4.3 g of the title compound: mp 106°–107° C., [α]$_D$−36.40 (1% in dimethylformamide), nmr (CDCl$_3$)δ 1.25(s), 3.60(s) and 5.10(s), and Anal. Calc'd. for C$_{31}$H$_{36}$N$_2$O$_6$: C, 69.91%; H, 6.81%; N, 5.26% and Found: C, 69.63%; H, 6.85%; N, 5.41%.

EXAMPLE 2

BENZYLOXYCARBONYL-ASPARAGINYL-(O-t-BUTYL)TRYOSYL-PHENYLALANINE METHYL ESTER (Z-Asn-Tyr(Bu$^t$)-Phe-OMe)

A mixture of Z-Tyr(Bu$^t$)-Phe-OMe (35 g, described in Example 1) and 5% palladium on carbon (3.5 g) in acetic acid (350 ml) was rapidly stirred under an atmosphere of hydrogen until the benzyloxycarbonyl group was removed. The mixture was filtered and the filtrate was evaporated. The residue was dried by azeotropic distillation with toluene and used as such in the next step. The residue of H-Tyr(Bu$^t$)-Phe-OMe HOAc was dissolved in dry, distilled dimethylformamide (240 ml). N-Ethylmorpholine (9.2 ml, 72 mmoles) was added followed by a solution of benzyloxycarbonyl-asparagine 4-nitrophenyl ester (28 g, 69 mmoles) in dimethylformamide (240 ml). The solution was stirred at 0° C. for four days and evaporated. The residue was triturated with diethyl ether, dissolved in methanol and precipitated with cold, saturated solution of aqueous sodium bicarbonate. The precipitate was collected, washed with water, dried and crystallized twice from methanol, giving 25 g of the title compound: mp 198° C. (dec.) and nmr(DMSO-D$_6$) δ 1.43(s), 3.60(s) and 5.03(s).

EXAMPLE 3

α,α-DIMETHYL-3,5-DIMETHOXYBENZYLOXYCARBONYL-(N$^6$-t-BUTOXYCARBONYL)-LYSYL-ASPARAGINYL-(O-t-BUTYL)TYROSYL-PHENYLALANINE METHYL ESTER (Ddz-Lys(Boc)-Asn-Tyr(Bu$^t$)-Phe-OMe)

A mixture of Z-Asn-Tyr(Bu$^t$)-Phe-OMe (2.5, described in Example 2) and 5% palladium on carbon (0.25 g) in acetic acid (25 ml) was rapidly stirred under an atmosphere of hydrogen until the benzyloxycarbonyl group was removed. The mixture was filtered and the filtrate was evaporated. The residue of H-Asn-Tyr(Bu$^t$)-Phe-OMe.HOAc was dried by azeotropic distillation with toluene. Dicyclohexylcarbodiimide (15 g, 7.5 mmoles) was added at once to a cold solution of Ddz-Lys(Boc)-OH (2.88 g, 6.14 mmoles) and 1-hydroxybenzotriazole (1.01 g, 7.5 mmoles) in dry, distilled dimethylformamide (25 ml). The mixture was stirred in an ice-bath for 30 min, then at room temperature for 90 min. The previous hydrogenolysed product dissolved in dry, distilled dimethylformamide (20 ml) containing N-ethylmorpholine (0.675 ml, 5.3 mmoles) was added to the above solution. The mixture was stirred overnight. After filtering, the filtrate was evaporated. The residue was crystallized as a gel first from ethyl acetate, then from methanol-isopropyl ether yielding 2.5 g of the title compound: mp 165°–167° C., nmr(DMSO-D$_6$) δ 1.25(s), 1.41(s) and 3.70(s), and amino acid analysis: Tyr(1.00), Phe(0.99), Asp(1.07) and Lys(0.92).

EXAMPLE 4

α,α-DIMETHYL-3,5-DIMETHOXYBENZYLOXYCARBONYL-(N$^6$-t-BUTOXYCARBONYL)LYSYL-ASPARAGINYL-(O-t-BUTYL)TYROSYL-PHENYLALANINE HYDRAZIDE (Ddz-Lys(Boc)-Asn-Tyr(Bu$^t$)-Phe—NHNH$_2$)

Hydrazine hydrate (5 ml, 0.1 moles) was added, dropwise to an ice-cold solution of Ddz-Lys(Boc)-Asn-Tyr(Bu$^t$)-Phe-OMe (2.5 g, 2.6 mmoles, described in Example 3) in methanol (50 ml). After the addition, the mixture was stirred at room temperature overnight. The precipitate was collected, washed with methanol and dried to give the title compound (1.6 g): nmr(DMSO-D$_6$) δ 1.25(s), 1.41(s) and 3.75(s), and amino acid analysis: Phe(1.00), Tyr(0.98), Asp(1.03) and Lys(0.88).

EXAMPLE 5

BENZYLOXYCARBONYL-D-TRYPTOPHYL-(N⁶-t-BUTOXYCARBONYL)LYSYL-(O-t-BUTYL)-THREONYL-PHENYLALANYL-(O-t-BUTYL)-THREONYL-(O-t-BUTYL)SERINE METHYL ESTER
(Z-D-Trp-Lys(Boc)-Thr(Bu$^t$)-Phe-Thr(Bu$^t$)-Ser(Bu$^t$)-OMe)

A mixture of Z-Lys(Boc)-Thr(Bu$^t$)-Phe-Thr(Bu$^t$)-Ser(Bu$^t$)-OMe (32.8 g, 0.033 mole, described in U.S. Pat. No. 3,917,578, cited above) and 5% palladium on carbon (1.65 g) in acetic acid (328 ml) was rapidly stirred under one atmosphere of hydrogen until the benzyloxycarbonyl group was removed. The mixture was filtered and the filtrate was evaporated to give a residue of H-Lys(Boc)-Thr(Bu$^t$)-Phe-Thr(Bu$^t$)-Ser(Bu$^t$)-OMe.HOAc. A mixture of benzyloxycarbonyl-D-tryptophan (14.5 g, 0.0428 mole) and 1-hydroxybenzotriazole (11.56 g, 0.0856 mole) in tetrahydrofuran (428 ml) at −10° C. and a mixture of dicyclohexylcarbodiimide (17.62 g, 0.0856 mole) in tetrahydrofuran (51 ml) were mixed together. The resulting mixture was stirred at 0° C. for one hr and at 25° C. for one hr. A solution of the above residue in tetrahydrofuran (150 ml) was adjusted to pH 7.5 with N-ethylmorpholine at 0° C. and added to the above mixture. The resulting mixture was stirred at 25° C. for 24 hr and filtered. The precipitate (A) was washed with ethyl acetate. The filtrate and ethyl acetate washings were washed with 1 N hydrochloric acid, water and saturated sodium bicarbonate, dried over magnesium sulfate and evaporated to give 8.8 g of the title compound and a mother liquor (B). Precipitate (A) was extracted with 3% methanol in chloroform. The extract was washed with 1 N hydrochloric acid, water and saturated sodium bicarbonate, dried over anhydrous magnesium sulfate and concentrated to give a precipitate (C) and mother liquor (D). Mother liquors (B) and (D) were concentrated to give another 10 g of the title compound. Precipitate (C) was triturated with 10% methanol in benzene and the insoluble material was discarded. The filtrate was concentrated to give another 15.9 g of the title compound: $[\alpha]_D$+20.7° (C=1, dimethylformamide), nmr(CDCl$_3$) $\delta$ 1.15(s), 1.25(s), 1.5(s), 3.65(s), 5.1(m) and 7.2(m), and amino acid analysis: Lys(1.05), Thr(2.01), Ser(1.07) and Phe(1.00).

EXAMPLE 6

α,α-DIMETHYL-3,5-DIMETHOXYBENZYLOXYCARBONYL-(N⁶-t-BUTOXYCARBONYL)LYSYL-ASPARAGINYL-(O-t-BUTYL)TYROSYL-PHENYLALANYL-D-TRYPTOPHYL-(N⁶-t-BUTOXYCARBONYL)LYSYL-(O-t-BUTYL)-THREONYLPHENYLALANYL-(O-t-BUTYL)-THREONYL-(O-t-BUTYL)SERINE METHYL ESTER
(Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)-OMe)

A mixture of Z-D-Trp-Lys(Boc)-Thr(Bu$^t$)-Phe-Thr(Bu$^t$)-Ser(Bu$^t$)-OMe (11.4 g, 0.0094 mole, described in Example 5) and 5% palladium on carbon (1.0 g) in acetic acid (221 ml) was rapidly stirred under one atmosphere of hydrogen until the benzyloxycarbonyl group was removed. The mixture was filtered and the filtrate was evaporated to give a residue of H-D-Trp-Lys(Boc)-Thr(Bu$^t$)-Phe-Thr(Bu$^t$)-Ser(Bu$^t$)-OMe acetate.

Tert-butyl nitrite (1.3 ml) was added to a solution of Ddz-Lys(Boc)-Asn-Tyr(Bu$^t$)-Phe-NHNH$_2$ (10.05 g, 0.0103 mole, described in Example 4) and 2.4 M hydrogen chloride in ethyl acetate (9.8 ml) in dimethylformamide (50 ml) at −15° C. The solution was stirred at −15° C. for 15 min and the solution was made neutral with N-ethyl-diisopropylamine (4.01 ml). A solution of the above residue of H-D-Trp-Lys(Boc)-Thr(Bu$^t$)-Phe-Thr(Bu$^t$)-Ser(Bu$^t$)-OMe acetate, N-ethyl-diisopropylamine (1.6 ml) in dimethylformamide (50 ml) was added to the solution at −15° C. The solution was stirred at −15° C. for one hr and at 25° C. for 20 hr and evaporated. The residue was chromatographed on silica gel (1.2 kg) using chloroform to 3% methanol in chloroform. The appropriate eluates were evaporated to give the title compound (9.8 g): nmr(CDCl$_3$) $\delta$ 1.10(s), 1.20(s), 1.25(s), 1.4(s), 1.45(s), 3.68(s), 3.70(s) and 7.2(m), and amino acid analysis: Lys(1.93), Thr(1.93), Phe(2.00), Ser(1.17), Asn(1.01), Tyr(0.95) and Trp(present).

EXAMPLE 7

α,α-DIMETHYL-3,5-DIMETHOXYBENZYLOXYCARBONYL-(N⁶-t-BUTOXYCARBONYL)LYSYL-ASPARAGINYL(O-t-BUTYL)TYROSYL-PHENYLALANYL-D-TRYPTOPHYL-(N⁶-t-BUTOXYCARBONYL)-LYSYL-(O-t-BUTYL)-THREONYLPHENYLALANYL-(O-t-BUTYL)-THREONYL-(O-t-BUTYL)-SERYL-7-AMINOHEPTANOIC ACID METHYL ESTER
(Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)-NH(CH$_2$)$_6$COOMe; V: X=(CH$_2$)$_2$ and Alk=Me)

A solution of Ddz-Lys(Boc)-Asn-Lys(Bu$^t$)-Phe-D-Trp-Lys(Boc)-Thr(Bu$^t$)-Phe-Thr(Bu$^t$)-Ser(Bu$^t$)-OMe (16.2 g, described in Example 6) and hydrazine hydrate (13.1 ml) in dimethylformamide (53 ml) was stirred at 25° C. for 20 hr and evaporated. The residue was triturated with water and the precipitate was collected and dried over phosphorus pentoxide to give 15.6 g of Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)-NHNH$_2$.

A solution of the latter compound (6.938 g), 2.19 M hydrogen chloride in ethyl acetate (3.995 ml), tert-butyl nitrite (0.484 ml) in dimethylformamide (18 ml) was stirred at −15° C. for 15 min. N-ethyl-diisopropylamine (1.495 ml) was added, followed by a solution of 7-aminoheptanoic acid methyl ester hydrochloride (0.958 g) and N-ethyldiisopropylamine (0.837 ml) in dimethylformamide (3 ml). The resulting mixture was stirred at −15° C. for one hr and at 25° C. for 20 hr and evaporated. The residue was chromatographed on silica gel (800 g) using 3% methanol in chloroform. The eluates were evaporated to give the title compound (6.2 g): $[\alpha]_D$ +6.80 (c=1, dimethylformamide), nmr(CDCl$_3$) $\delta$ 1.1(s), 1.15(s), 1.25(s), 1.3(s), 1.45(s), 3.6(s), 3.7(s) and 7.2(m), and amino acid analysis: Lys(1.93), Ser(1.04), Asp(1.04), Tyr(0.92), Thr(1.52) and Phe(2.0).

In the same manner, but replacing 7-aminoheptanoic acid methyl ester with an equivalent amount of 4-[(2-amino)ethylthio]butanoic acid ethyl ester or 3-[(3-amino)propylthio]propanoic acid methyl ester, the following compounds of formula V are obtained, respectively Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_2$—S—(CH$_2$)$_3$—COOEt and Ddz-Lys(Boc)-Asn-Tyr(-

Bu$^t$)-Phe-D-Trp-Lys(Boc)-Thr(Bu$^t$)-Phe-Thr(Bu$^t$)-Ser(Bu$^t$)—NH—(CH$_2$)$_3$—S—(CH$_2$)$_2$—COOMe.

EXAMPLE 8

α,α-DIMETHYL-3,5-DIMETHOXYBENZYLOXYCARBONYL-(N$^6$-t-BUTOXYCARBONYL)LYSYL-ASPARAGINYL-(O-t-BUTYL)TYROSYL-PHENYLALANYL-D-TRYPTOPHYL-(N$^6$-t-BUTOXYCARBONYL)LYSYL-(O-t-BUTYL)-THREONYLPHENYLALANYL-(O-t-BUTYL)-THREONYL-(O-t-BUTYL)SERYL-7-AMINOHEPTANOIC ACID (Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_6$—COOH; VI: X=(CH$_2$)$_2$)

A solution of the compound of formula V, Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_6$—COOMe (6.0 g, described in Example 7), in methanol (57 ml) and N sodium hydroxide (5.7 ml) was stirred at room temperature for 42 hrs. A solution of 5% citric acid was added until the solution reached pH 4 and water was added. The precipitate was collected, washed with water and dried to give the title compound, nmr(CDCl$_3$) δ 1.10(s), 1.15(s), 1.25(s), 1.30(s), 1.45(s), 3.7(s) and 7.2(m).

In the same manner but replacing Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_6$—COOMe with an equivalent amount of another compound of formula V described in Example 7, the following compounds of formula VI are obtained, respectively: Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_2$—S—(CH$_2$)$_3$—COOH and Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_3$—S—(CH$_2$)$_2$—COOH.

EXAMPLE 9

α,α-DIMETHYL-3,5-DIMETHOXYBENZYLOXYCARBONYL-(N$^6$-t-BUTOXYCARBONYL)LYSYL-ASPARAGINYL-(O-t-BUTYL)TYROSYL-PHENYLALANYL-D-TRYPTOPHYL-(N$^6$-t-BUTOXYCARBONYL)LYSYL-(O-t-BUTYL)-THREONYLPHENYLALANYL-(O-t-BUTYL)-THREONYL-(O-t-BUTYL)SERYL-7-AMINOHEPTANOIC ACID 4-NITROPHENYL ESTER (Ddz-Lys(Boc)-ASn-Tyr(Bu$^t$)-Phe-D-Trp-Lys(Boc)-Thr(Bu$^t$)-Phe-Thr(Bu$^t$)-Ser(Bu$^t$)—NH(CH$_2$)$_6$COO—C$_6$H$_4$—4—(NO$_2$); VII: X=(CH$_2$)$_2$)

A mixture of Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)-NH-(CH$_2$)$_6$-COOH (5.268 g, described in Example 8), 4-nitrophenyl trifluoroacetate (5.9 g) and pyridine (20 ml) in dimethylformamide (40 ml) was stirred at 50° C. for one hr and evaporated to 20 ml. Diethyl ether was added and the precipitate of the title compund (5.5 g) was collected: nmr(CDCl$_3$) δ 1.1(s), 1.2(s), 1.25(s), 1.45(s), 3.7(s) and 7.2(m), and amino acid analysis: Lys(2.00), Asp(0.92), Thr(1.50), Ser(1.03), Tyr(0.88) and Phe(1.88).

In the same manner, but replacing Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_6$—COOH with an equivalent amount of another compound of formula VI described in Example 8, the following compounds of formula VII are obtained, respectively: Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)-NH-(CH$_2$)$_2$-S-(CH$_2$)$_3$-COO-C$_6$H$_4$—4—(NO$_2$) and Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_3$—S—(CH$_2$)$_2$—COO—C$_6$H$_4$—4—(NO$_2$).

EXAMPLE 10

CYCLIC AMIDE OF (N$^6$-t-BUTOXYCARBONYL)LYSYL-ASPARAGINYL-(O-t-BUTYL)TYROSYL-PHENYLALANYL-D-TRYPTOPHYL-(N$^6$-t-BUTOXYCARBONYL)LYSYL-(O-t-BUTYL)THREONYL-PHENYLALANYL-(O-t-BUTYL)-THREONYL-(O-t-BUTYL)SERYL-7-AMINO-HEPTANOIC ACID

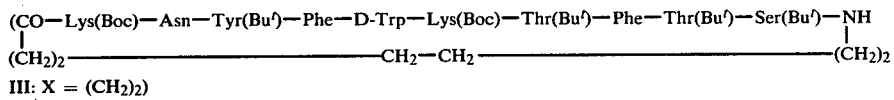

III: X = (CH$_2$)$_2$

A solution of Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—N-H—(CH$_2$)$_6$—COO—C$_6$H$_4$—4—(NO$_2$) (5.43 g, described in Example 9) in 50 ml of acetic acid: formic acid: water (7:1:2) was stirred at 25° C. for 24 hr and evaporated. The residue was dissolved in methanol (10 ml) and diethyl ether (200 ml) was added. The precipitate was dried over phosphorus pentoxide to give 4.8 g of the formate salt of the following compound of formula II, H-Lys(Boc)-Asn-Tyr(Bu$^t$)-Phe-D-Trp-Lys(Boc)-Thr(Bu$^t$)-Phe-Thr(Bu$^t$)-Ser(Bu$^t$)-NH-(CH$_2$)$_6$—COO—C$_6$H$_4$—4—(NO$_2$). A solution of the latter peptide (2.375 g) and pyridine (900 ml) was stirred at 45° to 50° C. for 3 hr and evaporated. The residue was chromatographed on silica gel (230 g) using 4% methanol in chloroform and the eluates were evaporated to give the title compound (0.96 g): [α]$_D$+9.21° (c=1, dimethylformamide), nmr(CDCl$_3$)δ 1.15(s), 1.25(s), 1.4(s), 1.45(s) and 7.2(m), and amino acid analysis: Lys(1.81), Asp(0.99), Thr(1.75), Ser(0.97), Tyr(0.92) and Phe(2.00).

In the same manner, but replacing Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$)$_6$—COO—C$_6$H$_4$—4—(NO$_2$) with an equivalent amount of another peptide of formula VII described in Example 9, the following peptides of formula III are obtained, respectively:

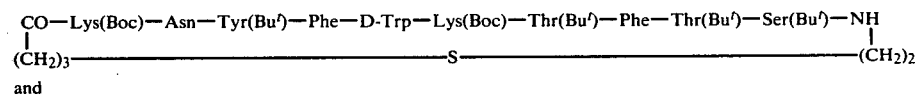

and

-continued

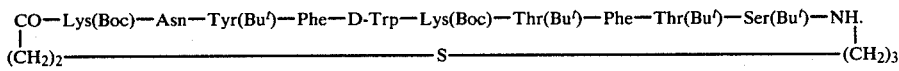

EXAMPLE 11

CYCLIC AMIDE OF LYSYL-ASPARAGINYL-TYROSYL-PHENYLALANYL-D-TRYPTOPHYL-LYSYL-THREONYL-PHENYLALANYL-THREONYL-SERYL-7-AMINOHEPTANOIC ACID

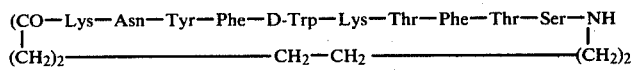

I: X = (CH$_2$)$_2$)

A solution of the peptide of formula III,

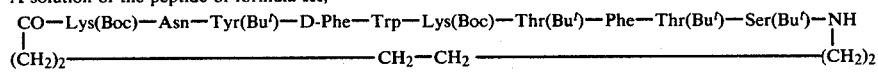

(1.1 g, described in Example 10), in trifluoroacetic acid (11 ml) and anisole (1.1 ml), under an atmosphere of nitrogen, was stirred at 25° C. for one hr and evaporated. The residue was chromatographed on silica gel using chloroform-methanol-32% acetic acid (5:3:1) and the eluants were evaporated to give a purified residue of the title compound (0.214 g). The residue was passed through a column of carboxymethyl cellulose using 0.1 M ammonium acetate and the eluates were evaporated to give the title compound as the acetate salt (0.181 g): uv max(MeOH) 289 ($\epsilon$=3475) and 280 mu($\epsilon$=4590) and amino acid analysis: Lys(2.08), Trp(0.58), Asp(1.00), Thr(1.78), Ser(1.03), Tyr(1.00) and Phe(2.02).

In the same manner, but replacing the starting material of formula III with another peptide of formula III described in Example 10, the following compounds of formula I are obtained, respectively:

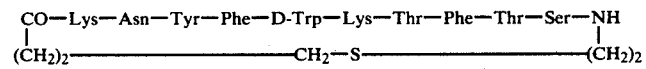

and

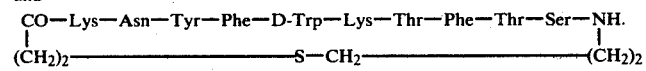

We claim:
1. A peptide of formula I

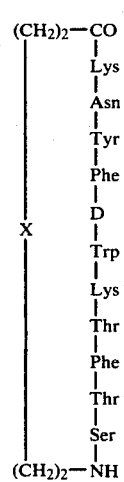

(I)

in which X is (CH$_2$)$_2$, or a therapeutically acceptable acid addition salt thereof.

2. A peptide of formula III

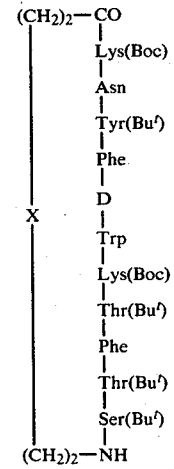

(III)

in which X is (CH$_2$)$_2$.

3. A formic acid addition salt of a peptide of formula II

H-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$.)$_2$—X—(CH$_2$)$_2$—COO—C$_6$H$_4$—4—(NO$_2$)    (II)

in which X is (CH$_2$)$_2$.

4. A peptide of formula VII

Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$.)$_2$—X—(CH$_2$)$_2$—COO—C$_6$H$_4$—4—(NO$_2$)    (VII)

in which X is (CH$_2$)$_2$.

5. A peptide of formula VI

Ddz-Lys(Boc)-Asn-Tyr(Bu$^t$)-Phe-D-Trp-Lys(Boc)-Thr(Bu$^t$)-Phe-Thr(Bu$^t$)-Ser(Bu$^t$)—NH—(CH$_2$.)$_2$—X—(CH$_2$)$_2$—COOH    (VI)

in which X is (CH$_2$)$_2$.

6. A pharmaceutical composition for treating acromegaly and managing diabetes in a mammal which comprises an effective amount of a compound of claim 1 and a pharmaceutical carrier.

7. A method of managing diabetes in a mammal which comprises administering to said mammal an effective amount of a compound of claim 1.

* * * * *